(12) United States Patent
Gosden et al.

(10) Patent No.: US 6,923,376 B2
(45) Date of Patent: Aug. 2, 2005

(54) ICONOGRAPHIC MEDICAL AND POPULATION SURVEY AND SYSTEM AND METHOD FOR USING THE SAME

(76) Inventors: Christine Gosden, 12 Baskervyl Close, Heswall, Wirral, CH60 8QL (GB); Derek Gardener, 30 Coniston Avenue Ashton-on-Makerfield, Wigan, Lancashire, WN4 8AY (GB)

(*) Notice: Subject to any disclaimer, the term of this patent is extended or adjusted under 35 U.S.C. 154(b) by 645 days.

(21) Appl. No.: 09/966,319

(22) Filed: Sep. 28, 2001

(65) Prior Publication Data

US 2002/0063739 A1 May 30, 2002

Related U.S. Application Data

(60) Provisional application No. 60/236,683, filed on Sep. 29, 2000.

(51) Int. Cl.⁷ .............................................. G06K 19/00
(52) U.S. Cl. ....................... 235/487; 235/375; 235/376; 345/418
(58) Field of Search ................................ 235/487, 375, 235/376; 345/418, 902, 971; 705/3, 4

(56) References Cited

U.S. PATENT DOCUMENTS

| | | | | |
|---|---|---|---|---|
| 5,772,585 A | * | 6/1998 | Lavin et al. | 600/300 |
| 5,911,132 A | * | 6/1999 | Sloane | 705/3 |
| 6,014,435 A | * | 1/2000 | Rosen | 345/744 |
| 6,022,222 A | * | 2/2000 | Guinan | 434/169 |
| 6,112,182 A | * | 8/2000 | Akers et al. | 705/2 |
| 6,247,004 B1 | * | 6/2001 | Moukheibir | 706/46 |
| 6,489,977 B2 | * | 12/2002 | Sone | 345/835 |

* cited by examiner

Primary Examiner—Steven S. Paik
(74) Attorney, Agent, or Firm—Whiteford, Taylor & Preston, LLP.; R. Christopher Rueppell; Gregory M. Stone

(57) ABSTRACT

A system for the collection of data about health problems, handicaps, water supplies, living conditions, and people at risk is disclosed. The system uses an iconographic, color-coded indicia to denote family members, dead children, major medical conditions, handicaps and treatments, and other data. Such iconographic, color-coded indicia are selectively positionable on an anonymous but individually coded survey form, from which a digital image is made and electronically transmitted to a searchable database storing a collection of such survey forms for purposes of providing ease of access to medical records and the development and implementation of palliative care, intervention, and prevention programs.

12 Claims, 7 Drawing Sheets

FIGURE 1

| No of Rooms? 11 | Total Number of Occupants? 12 | Was House Damaged? 13 | Sanitation 14 | Where does the water come from? 15 | | Location? 16 | FAMILY NO 17 |
|---|---|---|---|---|---|---|---|
| Grandparents (A) | Father's Father | Father's Mother | | Mother's Father | Mother's Mother 30 | | |
| | | | | 23 | | | |
| Parents (B) | | Father | | Mother 30 | | | |
| | | | | 22 | | | |
| Children (C) | o | o | o | o 30 | | Orphans (O) 21b | |
| | | | | 21a | | | |
| | | | | 21 | | | |

ICONOGRAPHIC MEDICAL AND POPULATION SURVEY AND SYSTEM AND METHOD FOR USING THE SAME

CROSS-REFERENCE TO RELATED APPLICATIONS

The present application is based upon and gains priority from U.S. Provisional Patent Application Ser. No. 60/236,683, filed Sep. 29, 2000 by the inventors herein and entitled "Iconographic Medical And Population Survey And System And Method For Using The Same," the specification of which is incorporated herein by reference.

BACKGROUND OF THE INVENTION

1. Field of the Invention

The invention disclosed herein relates generally to systems for the collection of medical and population survey data and, more particularly, to a system for the collection of data about health problems, handicaps, water supplies, living conditions, and people at risk using an iconographic, color-coded indicia to denote family members, dead children, major medical conditions, handicaps and treatments, and other data, such iconographic, color-coded indicia being selectively positionable on an anonymous but individually coded survey form, from which a digital image is made and electronically transmitted to a searchable database storing a collection of such survey forms for purposes of providing ease of access to medical records and the development and implementation of palliative care, intervention, and prevention programs.

2. Description of the Background

Epidemiological surveys are an often used tool to analyze medical and other data relating to the quality of life of large numbers of diverse individuals. The collection of such data may be a valuable tool for public health organizations, government officials, hospitals, and even individual health care providers in studying the wide-spread health effects of environmental contaminants, socioeconomic factors, family histories and genetics of segments of the population, political oppression, and any other factors that might tend to affect a person's health and welfare. By studying and understanding such effects of such external factors on the health and welfare of wide segments of a given population, public health organizations, government officials, hospitals, and individual health care providers are better equipped to adopt policies, programs, and care regimens that provide treatment and preventative intervention to persons who show greater risk of developing health problems, and to concentrate such efforts on wide populations where such epidemiological data indicates a need for more concentrated intervention. The conducting of such surveys requires direct interaction with the survey subjects, collecting often times highly sensitive medical and personal data. The collection of such sensitive data is critical to enabling an accurate survey that in turn may be used to identify medical risks and needs of large populations to in turn plan and implement appropriate programs to provide treatment and preventative intervention.

Unfortunately, many areas of the world have underdeveloped regions in which the collection of sophisticated epidemiological data is highly impractical due to illiterate populations, lack of communications and transportation infrastructures, cultural differences, language barriers, and geographically disparate (and at times nomadic) populations. Likewise, underdeveloped areas in which armed conflicts take place, including bombardment by chemical and biological weapons, result in large numbers of the population exhibiting grave health problems which reflect an extreme need for the development and implementation of plans for medical treatment and preventative intervention. However, in such areas that have be ravaged by the ruins of war, many members of the population have lost loved ones and themselves endured serious injury and medical ailments which are highly sensitive issues for persons to discuss, particularly with strangers attempting to assimilate survey data.

Such epidemiological surveys also have widespread applicability in industrialized nations, enabling the assimilation of such data among particular ethnic groups or populations displaying common socioeconomic factors to in turn plan and implement appropriate programs and policies to provide treatment and preventative intervention where needed.

Thus, a need exists to provide an epidemiological survey which may uniformly be used to collect data from widely diverse populations having various socioeconomic, cultural, genetic, ethnic, and economic characteristics, which fosters the collection of such data from a geographically diverse population into a common searchable database, and which may be effectively implemented to collect highly sensitive and emotionally charged data from persons while minimizing the emotional strain placed on the subject of the survey.

SUMMARY OF THE INVENTION

It is, therefore, an object of the present invention to provide an iconographic medical and population survey which avoids the disadvantages of the prior art.

It is another object of the present invention to provide an iconographic medical and population survey which may be universally implemented despite language barriers among varying populations.

It is yet another object of the present invention to provide an iconographic medical and population survey which diminishes the emotional strain placed on survey subjects in collecting sensitive medical and socioeconomic data.

It is still yet another object of the present invention to provide an iconographic medical and population survey which provides a digital, graphical image of survey results which may be electronically transferred to a centralized database.

In accordance with the above objects, an iconographic medical and population survey is provided which enables the collection of data about major health problems and handicaps, water supplies, living conditions, and people at risk, which overcomes the problems of illiteracy of survey subjects by allowing household members to use representative colored pictographic icons to denote family members, dead children, major medical conditions, handicaps and treatments. Exposures to toxic substances, information about water, sanitation, geographical location, socioeconomic status and family relationships and orphans are all clearly demonstrated on a single, graphical form from which data can easily be understood, extracted, and used as the immediate database on which to structure medical programs, help and treatment. Such a single form format thus enables the depiction of survey results from entire households, including children, elderly, and babies, in order to avoid bias. The survey form preferably also depicts dead family members involved in conflicts along with their cause of death, and provides information relating to each individual's exposure to various, specifically identified toxins and/or chemical agents. The survey of the instant invention thus provides a very simplified means of collecting and organizing highly relevant, sophisticated, and specific epidemiological data.

Moreover, the survey of the instant invention enables the surveying of the entire extended family beyond the household itself in the parental generation level. Such collection of data relating to extended family members allows the collection of information about: (i) the broader population base, such as people lost (e.g., displacement camps); (ii) causes of death of people lost in conflicts; (iii) social structures; (iv) disease frequencies and prevalence prior to a conflict/survey; (v) knowledge of preexisting medical conditions in the population being surveyed which allow comparison with generations conceived after the event; and (vi) lethal effects which otherwise would not have been realized because the victims would otherwise have been unable to report such effects.

The graphical survey data form is copied electronically in digital video format and transmitted electronically to a centralized database housing numerous graphical survey data forms relating to diverse members of a given population, while the original survey data form is provided to a local medical team for immediate medical use. Geosatellite survey data is optionally used to identify particular households in geographical regions that are home to conflict by assigning an arbitrary alpha-numeric designation to each home participating in the survey, which in turn coordinates with a particular geographical coordinate reflected on the geosatellite survey data.

Particular problems in conflict regions, and the fear of danger associated with those problems, require that such a survey and data collection process be transparent to allay the fears of the survey participants. Using such an arbitrary code to identify individual households and household members participating in the survey assures anonymity of each survey participant, while providing data which if made available (such as to individual physicians who might treat survey participants) can associate such data with specific individuals in order to provide optimized and particularized medical treatment and intervention programs. Further, enabling survey participants to interactively participate in the survey by independently placing color-coded pictographic icons on a survey sheet, as opposed to answering highly sensitive and emotional questions from an unfamiliar surveyor, greatly minimizes the emotional stress a participant will endure in providing such sensitive information, while their direct participation and interaction with the interviewer provides for the collection of the maximum amount of information and ensures accuracy of that information. Likewise, such direct participation on the part of the survey subjects enhances trust of the survey on the part of the participant, allowing the survey participants to see the information collected about them as it is collected. Moreover, the use of pictorial icons instead of textual questions directed to highly disparate members of a population allows the survey of the instant invention to overcome multicultural, multilingual, illiteracy, and cultural sensitivity barriers that might otherwise exist in the administration of a strictly oral and/or textual survey. Further, to ensure that such an epidemiological survey may be used as an effective tool for widespread analysis and development of treatment and intervention programs, the survey of the instant invention is compatible with existing epidemiological databases, e.g., age/sex ratios, including by way of example EipInfo 2000 and other databases such as ACCESS.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 1 is a schematic representation of a blank family data entry form of the instant invention.

FIG. 5 is a schematic representation of a completed family data entry form for a particular family.

DETAILED DESCRIPTION OF THE PREFERRED EMBODIMENTS

Figure 2:
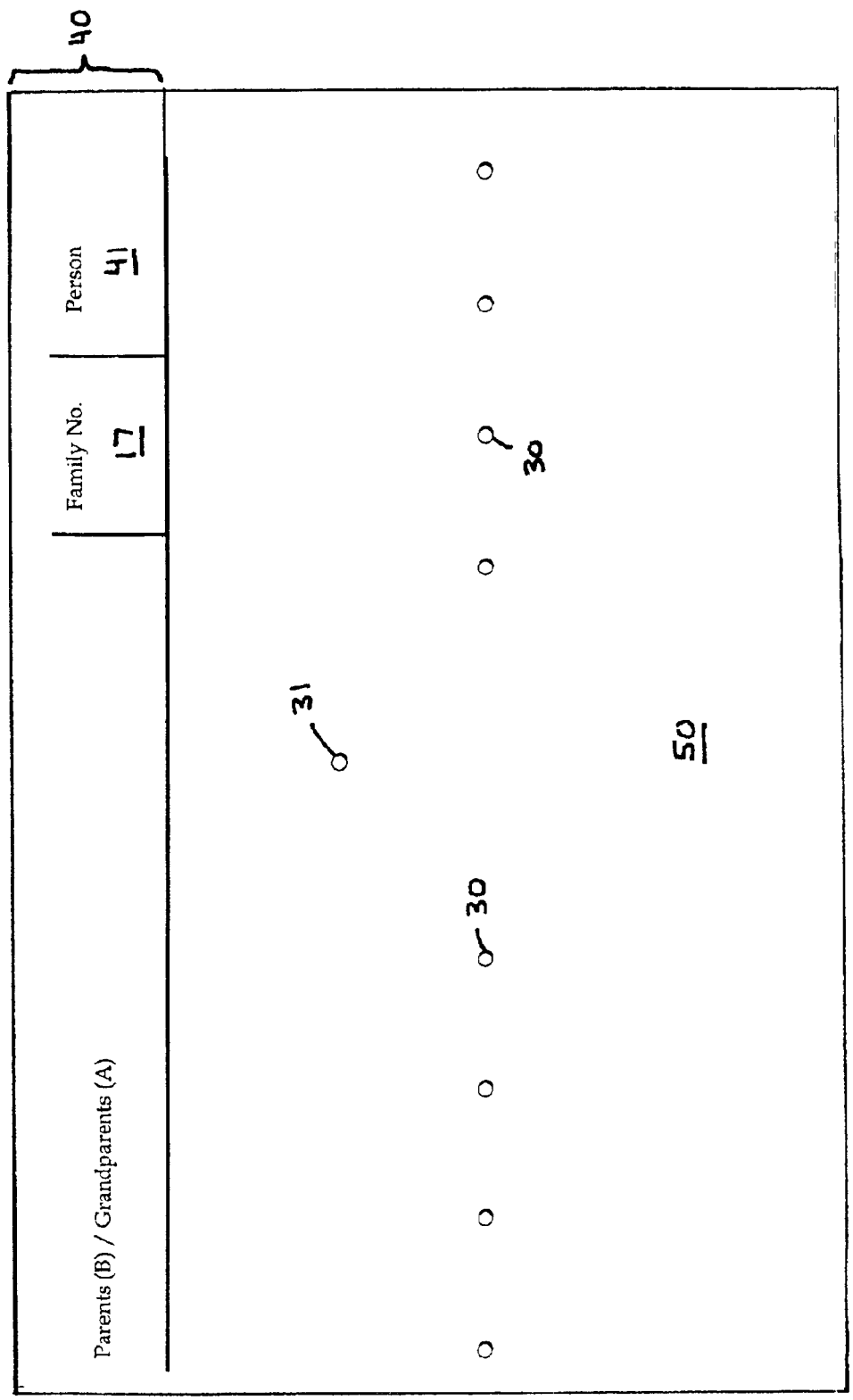
FIG. 2 is a schematic representation of a blank individual data entry form of the instant invention.

The iconographic medical and population survey of the instant invention provides a number of functions, as follows. First, the survey gathers information about living quarters of each household, whether the living quarters were damaged in conflicts, and any potential continuing contamination by ascertaining the sources of their water supply (either artesian or local well), sanitation and environment. Second, the survey ascertains the structure of the households, including how many people in the household are employed and earning a salary, how many households comprise single parent families, how many orphans are boarding with a family in each household, how many generations of people are present in each household, and how many people have sleeping accommodations in each room. Third, the survey assesses principal illnesses as defined by the survey participants themselves, as well as healthcare needs (e.g., how many people are blind, how many need wheelchairs, how many are mentally and/or physically handicapped, how many are bomb, shell, or mine victims, and whether or not the persons are in contact with doctors or medical teams). Fourth, the survey identifies people at risk, such as women of reproductive age in areas having higher-than-normal concentrations of birth defects, exposures and risks for cancer, children and young adults with mental and/or physical handicaps who may benefit from special education services, workshops, and care programs, and persons having higher-than-normal suicide risks who may benefit from psychological intervention and aid programs. Fifth, the survey investigates the population structure existing following an armed conflict or other disaster, and the age and sex distribution of those who have died and of the survivors to prioritize active health intervention and research programs which will benefit survivors.

The survey system of the instant invention comprises a series of data entry forms and a series of pictographic icons which may be placed by a survey participant on a data entry form to indicate such participant's answers to the surveyor's questions. Allowing the survey participants to take such direct control of the survey assures them that the information being collected is accurate, that it addresses their health needs, and that they can use it as a method of communication to make their most immediate concerns known to medical teams.

As shown in FIG. 1, a family data entry form is provided for each home in the survey which provides a Home Description Array 10 and a Home Iconographic Data Array 20. Home Description Array 10 provides a number of fields describing physical qualities of the participant's home, and preferably includes the following fields: (i) Number of Rooms field 11 for indicating the number of rooms in the home; (ii) Total Number of Occupants field 12 for indicating the total number of occupants in the home; (iii) House Damage Field 13 for indicating whether or not the home was damaged after an attack or other disaster and not yet properly repaired; (iv) Sanitation Field 14 for indicating what type of sanitation is present in the home; (v) Water Source Field 15 for indicating the source of water supplied to the home (i.e., artesian or local well), (vi) Location Field 16 for indicating the alpha-numeric grid coordinate corresponding to geosatellite coordinate information; and (vii) Family Number Field 17 for assigning an arbitrary number to the family being surveyed.

Iconographic Data Array 20 comprises a first generation visual data array 21, a second generation visual data array 22, and a third generation visual data array 23. First generation visual data array 21 is preferably segmented into a first window 21a relating to first generation individuals within a home and relating to the second generation individuals indicated in second generation visual data array 22, and a second window 21b relating to orphaned children living in the same home. A series of positioning markers 30 are preferably provided in each visual data array 21 through 23 to aid a survey participant in placing pictographic icons on the data form.

As shown in FIG. 2, an adult individual data entry form is also provided for each adult individual in the survey which provides an Individual Description Array 40 and an Individual Iconographic Data Array 50. Individual Description Array 40 provides Family Number Field 17 indicating the arbitrary number assigned to the family being surveyed on the family data entry form, and a Person Number Field 41 for assigning an arbitrary number to the individual adult being surveyed. Individual Iconographic Data Array 50 comprises a single visual data array having a series of positioning markers 30 and 31. Positioning marker 31 preferably indicates a position at which a survey participant would place visual data pertaining to themselves, while positioning markers 30 preferably indicate positions at which a survey participant would place visual data pertaining to their siblings, both living and dead.

Figure 3:
FIG. 3 is a depiction of the visual iconographic logic of the instant invention for denoting persons who are the subject of the survey.
Figure 4:
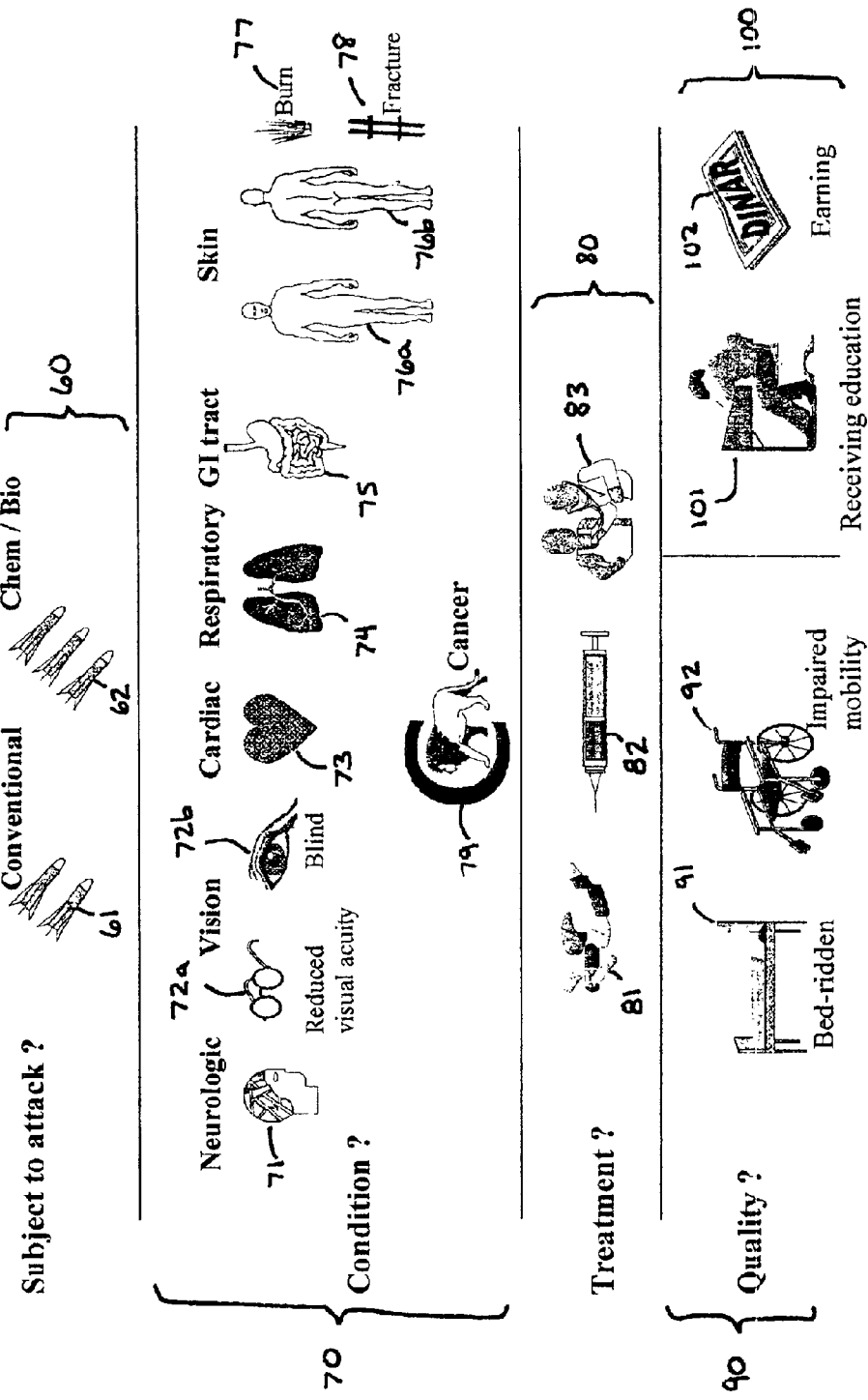
FIG. 4 is a depiction of the visual iconographic logic of the instant invention for denoting various conditions of the persons who are the subject of the survey.

As shown in FIGS. 3 and 4, the particular pictographic icons to be used in the system of the instant invention comprise varying forms. While the precise design of the icons may vary without departing from the spirit and scope of the instant invention, the key functional features which are key elements of the system of the instant invention are as follows.

It is important that the icons be color-coded, such that multiple icons of a particular group (e.g., adult males) may be readily distinguished from one other to associate each member of that group with a particular subgroup (e.g., living, deceased, in home, etc.), and that such distinction be readily discernable in a digital reproduction of a completed data survey sheet to maintain the necessary distinctions among strictly visual data.

As shown in FIG. 3, it is necessary that the icons referring to individuals be provided in the following groups: adults, children, infants (i.e., under 1 year), stillborn, and miscarriages. Each group may in turn be separated into subgroups by color-coding, whereby a single color depicts one of the following subgroups: (i) persons normally resident in the home at the time of the survey; (ii) persons normally resident outside of the home at the time of the survey; and (iii) persons who are deceased. Optionally, a single color may be used to identify a particular sex within each group, e.g., a first color representing adult males normally resident in the home, and a second color representing adult females normally resident in the home, and colors may be combined within a single group, such as a flesh color human infant icon superimposed over a second color background representing infant males normally living in the household, and third color human infant icon superimposed over such second color background representing deceased infant males. In the most preferred embodiment of the instant invention, the following color-coding scheme is utilized: (i) a first color indicating adult males within the home, child males within the home, and infant males within the home or deceased; (ii) a second color indicating adult females within the home, child females within the home, and infant females within the home or deceased; (iii) a third color indicating adult males and females outside of the home, and child males and females outside of the home; (iv) a fourth color indicating male infants outside of the home; (v) a fifth color indicating female infants outside of the home; and (vi) a sixth color indicating deceased adult males and females, deceased child males and females, deceased infant males and females, stillborn babies, and miscarriages.

FIG. 4 likewise provides a visual descriptive iconography for enabling a survey participant to indicate each person's health history and socioeconomic data. Such visual, pictographic icons are preferably provided in five groups, namely, weapons attack icons 60, medical condition icons 70, medical treatment icons 80, mobility icons 90, and socioeconomic icons 100. Weapons attack icons 60 preferably comprise a first icon 61 indicating a conventional weapons attack, and a second icon 62 indicating a chemical/biological weapons attack. Medical condition icons 70 preferably comprise a first icon 71 indicating a neurological disorder, a second icon 72a indicating reduced visual acuity, a third icon 72b indicating blindness, a fourth icon 73 indicating a cardiac disorder, a fifth icon 74 indicating a respiratory disorder, a sixth icon 75 representing a gastrointestinal disorder, a seventh icon representing a front 76a and back 76b of a human body, an eighth icon 77 representing a burn injury, a ninth icon 78 representing a fracture injury, and a tenth icon 79 representing cancer. Medical treatment icons 80 preferably comprise a first icon 81 representing oral medications, a second icon 82 representing injection medications, and a third icon 83 representing physician care. Mobility icons 90 preferably comprise a first icon 91 representing a bed-ridden condition, and a second icon 92 representing impaired mobility less than a bed-ridden condition. Finally, socioeconomic icons 100 comprise a first icon 101 representing a person receiving education, and a second icon 102 representing a person employed and receiving a salary. Additional icons may optionally be added to denote other various medical conditions, environmental exposures, socioeconomic conditions, and the like.

Figure 5:
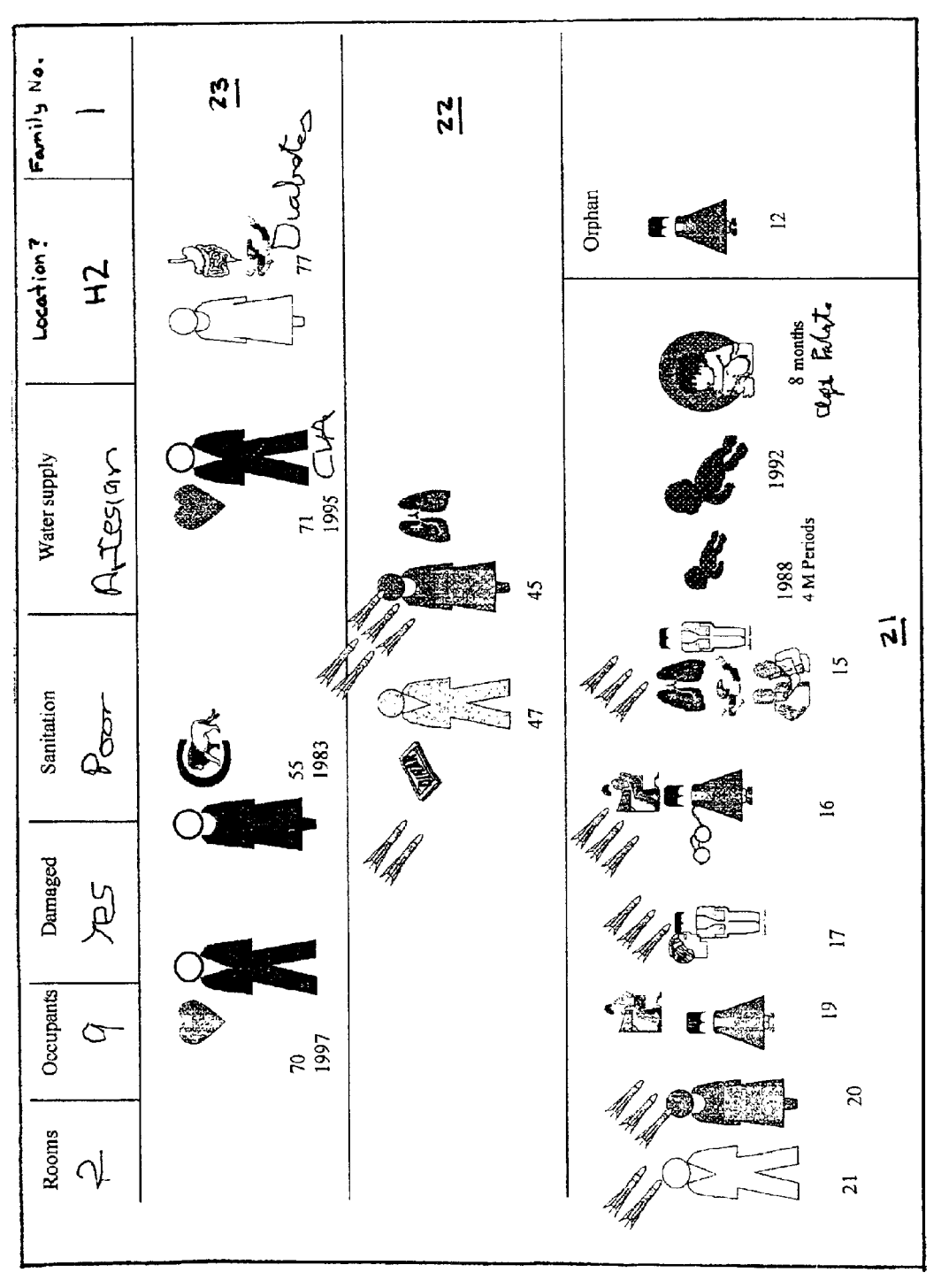

FIG. 5 is an exemplary representation of a completed family data entry form. Applying the iconographic system described above, FIG. 5 depicts a home having 2 rooms and 9 occupants, the home having sustained damage from an attack, with poor sanitation and an artesian water supply. As will be described in further detail below, the home location corresponds to a grid coordinate H2 which represents a specific geographical coordinate region obtained from geosatellite positioning data. Second generation visual data array 22 indicates that a 47 year old adult male is living at the home and is employed and earning a salary, and was victim to a conventional weapons attack. Also depicted in second generation visual data array 22 is a 45 year old adult female, living at the home, who was victim to both a conventional weapons and a chemical/biological weapons attack and is suffering from a respiratory disorder. Third generation visual data array 23 indicates that the adult male's parents are both deceased, the male having died at age 70 from a heart-related ailment, and the female having died at the age of 55 from cancer. Also indicated in third generation visual data array 23 is the fact that the adult female's father died at age 71 from a heart-related ailment, and that her mother, age 77, is alive and suffering from diabetes and a gastrointestinal disorder, and is receiving oral medication. First generation visual data array 21 indicates the following: (i) a 21 year old male is living outside of the home and was a victim of a conventional weapons attack; (ii) a 20 year old female is living in the house and was a victim of a chemical/biological weapons attack; (iii) a 19 year old female is living in the house and receiving formal education; (iv) a 17 year old male is living in the house, suffers from a neurological disorder, and was a victim of a chemical/biological weapons attack; (v) a 16 year old female is living in the house, is receiving formal education, suffers from a visual impairment, and was a victim of a chemical/biological weapons attack; (vi) a 15 year old male is living in the house, is receiving the care of a physician and oral medications, suffers from a respiratory ailment, and was a victim of a chemical/biological weapons attack; (vii) a pregnancy was prematurely terminated after 4 months; (viii) an infant was stillborn; (ix) an infant female is living in the house and suffers from a cleft palate; and (x) a 12 year old female orphan is living in the house.

Figure 6:
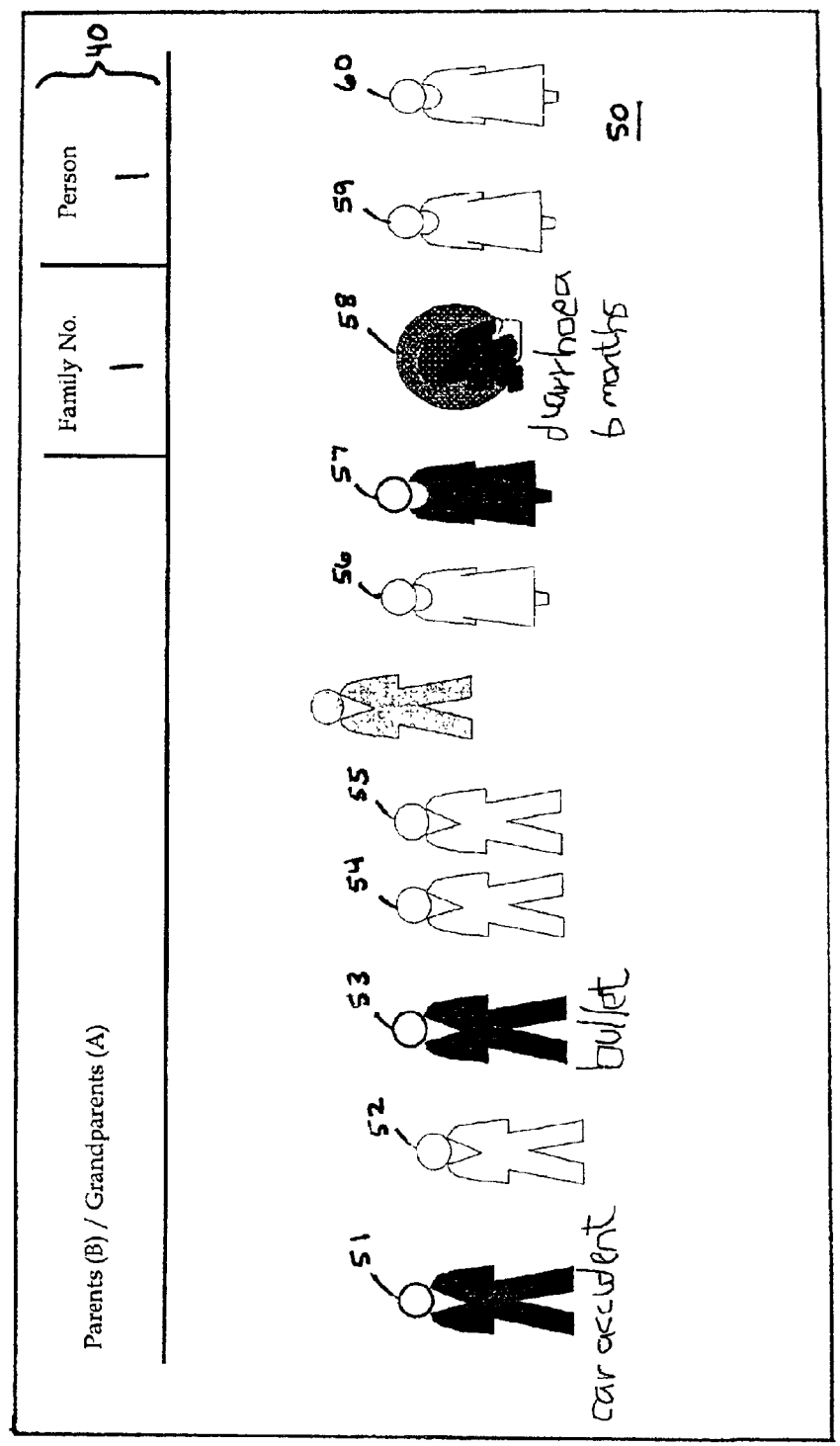
FIG. 6 is a schematic representation of a completed individual data entry form for a particular individual noted in FIG. 5.

From the second generation visual data array indicating a living male and female on the family data entry form of FIG. 5, an adult visual data entry form is shown in FIG. 6 depicting the siblings of the male second generation adult. As shown in the Individual Description Array 50 of FIG. 6, the male second generation adult of FIG. 5 has the following siblings: (i) an adult brother 51 who was killed in an auto accident; (ii) an adult brother 53 who was killed in a shooting; (iii) three adult brothers 52, 54, and 55 who are living outside of the home of the male second generation adult of FIG. 5; (iv) an adult sister 57 who is deceased; (v) an infant sister 58 who died at age 6 months from diarrhea; and three adult sisters 56, 59 and 60 who are living outside of the home of the male second generation adult of FIG. 5.

In order to provide an alphanumeric designation relating to a geographical location for each home surveyed, prior to initiating a survey, a map depicting the geographical area to be surveyed is divided into a grid, and each location or square on the grid is given a particular alphanumeric designator; for example, each column of the grid may be labeled with a letter, and each row of the grid may be labeled with a number. Preferably, a digital map is used which digital image may be easily divided into a grid having defined alpha-numeric designators for each grid element. Thus, by way of example, any home that lies on the map that is within the eighth row, second column would receive a "LOCATION" indicator "H2" in Location Field 16. Thereafter, as any home in area H2 is surveyed, it is given a "FAMILY NUMBER" indicator relating simply to the order in which the houses in that particular area are surveyed, which indicator is reflected in Family Description Array 10 in Family Number Field 17. Likewise, as each adult in each home surveyed is then individually surveyed to determine the status of their siblings, a "PERSON NUMBER" indicator relating to the specific individuals in the home is reflected in Individual Description Array 40 in Person Number Field 41. Specific geosatellite positioning data may optionally be linked to the particular family number in a given area, and the particular person number in a home, in order to enable the linking of a specific family data form with a given family (and a specific individual data form with an individual) for purposes of enabling local doctors and government officials to provide particularized care to those in need.

Figure 7:
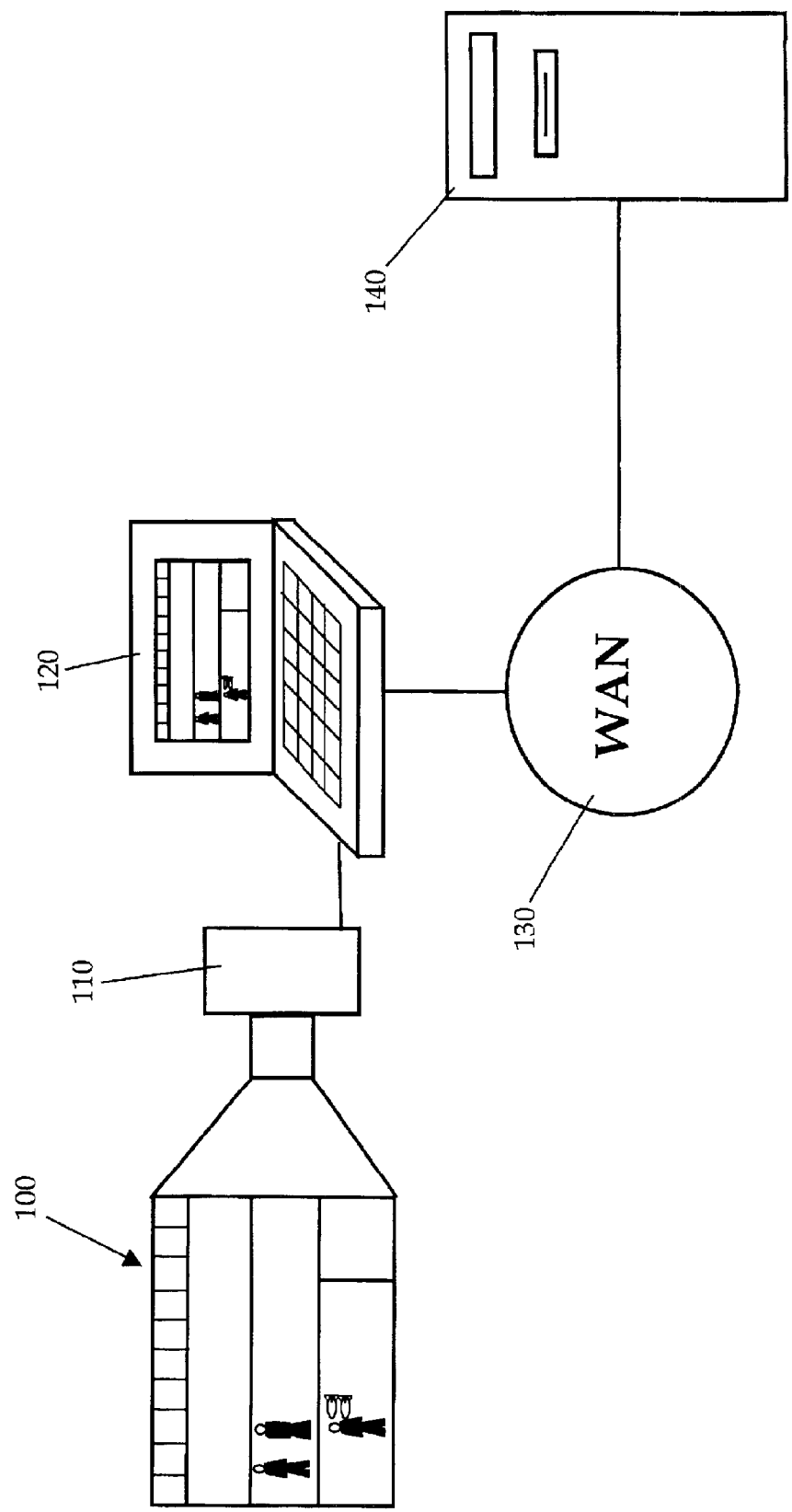
FIG. 7 is a schematic view of the system for enabling the assimilation of visual data from remote survey participants.

As explained briefly above, the visual iconographic survey of the instant invention enables surveys to be taken from widely diverse populations irrespective of barriers that exist due to illiteracy, cultural differences, language barriers, and the like. However, in order for the survey to be optimally useful, it is necessary that the visual survey data collected have the ability to be set in digital form so that (i) it may easily be transferred via remote communications networks to other potential users of the survey data; and (ii) may be easily integrated with a searchable database to allow optimal analysis of large collections of such survey data. As shown in FIG. 7, in order to enable the electronic collection and dissemination of such data, the survey system of the instant invention also provides a means 110 for creating an electronic file including a digital image of the visual data placed on a data form by a survey participant, along with textual identifiers indicating the information in Description Arrays 10 and 40. Such means 110 may comprise a digital camera, video camera, scanner, or any other digital image capturing device which may transmit, either remotely or through direct communications link, such digital image to a storage device 120 such as a memory stored on a laptop computer. The storage device in turn is in communication with means for transferring such digital data to a remote server 140, such transferring means preferably comprising a wide area network such as the Internet, or any other remote communications means, such as satellite transmission. Server 140 preferably stores in a memory held within server 140 a database for collecting the visual iconographic data from a number of remote sources, and may optionally provide limited access to remote users to access the database for purposes of data analysis. In an alternate embodiment of the invention, the digital image captured by digital imaging means 110 may be stored on any small, readily portable and duplicatable digital storage media (e.g., video cassettes, magnetic storage media or solid state) and physically transported to server 140, thus eliminating any need for computing facilities at the survey locations. Further, whether stored on a portable digital storage device and physically transported to server 140 or stored on a memory storage device on a laptop computer or the like and electronically transmitted to server 140, the original survey forms may be easily reproduced from the electronic versions for use in the field.

It may thus be seen that the system and method of the instant invention provide an improved epidemiological survey which provides medical data for immediate use, and which provides the following advantages: (i) the system is sensitive to population, culture, and region; (ii) the system allows participants to describe their own health problems, which information may be corroborated by doctors; (iii) the system provides a sensitive data collection method for deaths, miscarriages, infant loss, reproduction and infertility, and their consequences, e.g., number of wives taken, number of miscarriages and dead children; (iv) the system highlights people with special risks, multiple handicaps and needs; (v) the system provides a sensitive and sympathetic study of patterns of loss, physical and mental problems; (vi) the system combines human interaction with self-directed examination; (vii) the system identifies major medical and household problems at a glance; (viii) the system provides information about water, sanitation and socioeconomic factors; (ix) the system provides information about family relationships and orphans; (x) the system provides information about age/sex distribution of living and dead populations; (xi) the system provides information about frequency and types of medical conditions, age, sex and geographical distributions; (xii) the system provides generational information and familial disease risks; (xiii) the system provides information about extended family members; (xiv) the system gives information about people who died and survivors; (xv) the system allows construction of population structure, deaths, and damaged housing; (xvi) the system provides integration with digital maps for population/geographic distributions; (xvii) the system provides information about socioeconomic conditions, number of rooms, water and sanitation, how many persons to a room, source of water, and family income; (xix) the system allows people to communicate about major mental and physical problems; (xx) the system allows ascertainment of information about children over the age of 8 years who are not in school, e.g., with behavioral disorders or as family source of income; (xxi) the system provides a hard copy of a data survey sheet which households, doctors, and data survey teams can update; (xxii) the system provides for the interaction of the visual data and a database for survey analysis; (xxiii) the system provides a digital video of clinical cases which can be related to individuals in the household survey, with all imaging linked to a database of households, relatives and family structures; (xxiv) the system provides an unbiased ascertainment by geosatellite reference and grid squares, such that people can remain anonymous; (xxv) the system enables medical personnel to check the data forms and determine which cases are severe, determine the needs of orphans, patients, and households, and instigate special treatments; (xxvi) the system uses simplistic visual icons which may readily be modified for particular cultures; (xxvii) the system allows for the prioritization for palliative care and other programs; (xxviii) the system allows easy access to visual records of medical care and patient evaluations; (xxix) the system aids the design of intervention and prevention programs; and (xxx) the system aids the design and running of trials to assess the efficacy of different interventions. The survey system of the instant invention also lays the foundation for further studies, including palliative care and other programs, medical care and patient evaluations, prevention programs, trials to assess the efficacy of different interventions, and a record of exposures in relation to treatment needs and disease consequences.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

We claim:

1. An iconographic medical and population survey kit comprising:
    at least one family data entry form comprising a home description array having a plurality of physical home quality data fields and a home iconographic data array;
    at least one individual data entry form comprising an individual description array and an individual iconographic data array; and
    a plurality of color-coded iconographic symbols configured for attachment to said family data entry form and said individual data entry form, said iconographic symbols comprising people-representative iconographic symbols and condition-representative iconographic symbols.

2. The iconographic medical and population survey kit of claim 1, said physical home quality data fields further comprising:
    a room count data field;
    a home occupant data field;
    a house damage data field;
    a sanitation description data field;
    a water source data field;
    a geographic location data field; and
    a family identification code data field.

3. The iconographic medical and population survey kit of claim 1, said home iconographic data array on said family data entry form further comprising:
    a first generation visual data array;
    a second generation visual data array; and
    a third generation visual data array.

4. The iconographic medical and population survey kit of claim 3, said third generation visual data array further comprising:
    a related children visual data array; and
    an orphaned, in-home children visual data array.

5. The iconographic medical and population survey kit of claim 1, said individual description array on said individual data entry form further comprising a plurality of individual identification data fields.

6. The iconographic medical and population survey kit of claim 5, said individual identification data fields further comprising:
    a family identification code data field; and
    an individual identification code data field.

7. The iconographic medical and population survey kit of claim 6, said family identification code data field also being provided in said home description array in said family data entry form.

8. The iconographic medical and population survey kit of claim 1, said people-representative iconographic symbols further comprising:
    an adult symbol;
    a child symbol;
    an infant symbol;
    a stillborn symbol; and
    a miscarriage symbol.

9. The iconographic medical and population survey kit of claim 8, wherein said adult symbol, said child symbol, and said infant symbol are further color-coded to distinguish among individuals alive and normally resident in the home of a person being surveyed, alive and normally resident outside the home of the person being surveyed, and persons who are deceased.

10. The iconographic medical and population survey kit of claim 9, wherein said adult symbol, said child symbol, and said infant symbol are further color-coded to distinguish among male and female individuals.

11. The iconographic medical and population survey kit of claim 1, said condition-representative iconographic symbols further comprising:
    a weapons attack victim symbol;
    a medical condition symbol;
    a medical treatment symbol;

a mobility symbol; and a socioeconomic status symbol.

12. A method for conducting an iconographic medical and population survey comprising the steps of:

provide to the survey subject:

at least one family data entry form comprising a home description array having a plurality of physical home quality data fields and a home iconographic data array;

at least one individual data entry form comprising an individual description array and an individual iconographic data array; and a plurality of color-coded iconographic symbols configured for attachment to said family data entry form and said individual data entry form, said iconographic symbols comprising people-representative iconographic symbols and condition-representative iconographic symbols;

collecting from said survey subject completed family data entry and individual data entry forms with iconographic symbols placed thereon;

obtaining an electronic image of each of said collected, completed family data entry and individual data entry forms with iconographic symbols placed thereon; and storing said electronic images in an electronic storage device.

* * * * *